United States Patent [19]

Meyer et al.

[11] 3,943,144

[45] Mar. 9, 1976

[54] CERTAIN THIADIAZOLYL PHOSPHORUS ACID ESTERS

[75] Inventors: Willy Meyer, Basel; Beat Böhner, Binningen; Dag Dawes, Pratteln, all of Switzerland

[73] Assignee: Ciba-Geigy Corporation, Ardsley, N.Y.

[22] Filed: Apr. 12, 1974

[21] Appl. No.: 460,623

[30] Foreign Application Priority Data
Apr. 19, 1973  Switzerland.......................... 5758/73
Apr. 19, 1973  Switzerland.......................... 5759/73
Feb. 18, 1974  Switzerland.......................... 2218/74

[52] U.S. Cl...... 260/302 E; 260/302 D; 260/553 E; 424/200
[51] Int. Cl.² ....................................... C07D 285/08
[58] Field of Search .............................. 260/302 E

[56] References Cited
UNITED STATES PATENTS

| | | |
|---|---|---|
| 3,666,768 | 5/1972 | Barker et al. .................... 260/302 E |
| 3,784,554 | 1/1974 | Barker............................ 260/302 E |
| 3,801,586 | 4/1974 | Barker et al. ................... 260/302 E |

FOREIGN PATENTS OR APPLICATIONS

| | | | |
|---|---|---|---|
| 652,050 | 12/1964 | Belgium .......................... | 260/302 E |

*Primary Examiner*—R. Gallagher
*Attorney, Agent, or Firm*—Harry Falber

[57] ABSTRACT

New 1,2,4-thiadiazoles substituted with a phosphorus containing radical and corresponding to the formula

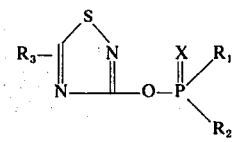

are disclosed. In this formula $R_1$ is alkyl or alkoxy, $R_2$ represents alkoxy, alkylthio, amino, alkylamino, or dialkylamino, $R_3$ stands for hydrogen, alkyl, aralkyl or cyclo-alkyl, and X is oxygen or sulphur. Such compound may be manufactured according to known methods and exibit a pesticidal especially an insecticidal and acaricidal activity.

7 Claims, No Drawings

CERTAIN THIADIAZOLYL PHOSPHORUS ACID ESTERS

The present invention provides 1,2,4-thiadiazolyl-(3)-phosphates, -phosphonates, -thiophosphates, -thiophosphonates or -thiophosphoric amides, a process for their manufacture, and a method for their use in pest control.

The 1,2,4-thiadiazolyl derivatives have the formula

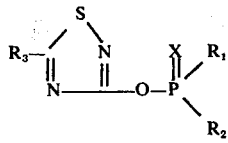

wherein $R_1$ represents alkyl or alkoxy, $R_2$ represents alkoxy, alkylthio, amino, alkylamino or dialkylamino, $R_3$ represents hydrogen, alkyl, aralkyl or cycloalkyl, and X represents oxygen or sulphur.

The alkyl, alkoxy, alkylthio, alkylamino and dialkylamino groups represented by $R_1$, $R_2$ and $R_3$ can be branched or straight-chain, substituted or unsubstituted, and contain 1 to 18, but especially 1 to 5, carbon atoms in the chain. Preferred substituents are fluorine, chlorine, methoxy, methylthio, cyano and/or nitro.

Examples of such groups include: methyl, methoxy, methyl-thio, ethyl, ethoxy, ethylthio, n-propyl, n-propoxy, iso-proxy, propylthio, isopropyl, n-butyl, isobutyl, sec. and tert. butyl, n-pentyl, and isomers thereof, n-pentoxy, n-penthylthio, methyl-amino, dimethylamino, n-propylamino, isopropylamino, allyl, methallyl, trifluoromethyl, 3-chloroallyl, trichloromethyl, cyanomethyl, 2-cyanoethyl, methoxymethyl, methylthiomethyl, and 2-chloroethyl. Suitable cycloalkyl groups are in particular monocyclic radicals with 3 to 8 ring carbon atoms that can be substituted by lower alkyl and/or bonded through a methylene or polymethylene bridge member. Examples of such radicals are: cyclopropyl, cyclobutyl, cyclopentyl, cyclohexyl. By aralkyl groups are meant chiefly unsubstituted benzyl or phenethyl or benzyl or phenethyl that is monosubstituted or polysubstituted by e.g. chlorine, bromine, nitro, methyl, methoxy and/or methylthio; in the case of poly-substitution the substituents may be the same or different.

Preferred compounds on account of their action are those of the formula I wherein $R_1$ represents methyl, ethyl, methoxy or ethoxy, $R_2$ represents methoxy, ethoxy, n-propoxy, n-propylthio, amino, methylamino, isopropylamino or n-propyl-amino or dimethylamino, $R_3$ represents hydrogen, alkyl with 1 to 5 carbon atoms, benzyl, phenethyl, cyclopentyl or cyclohexyl, and X represents oxygen or sulphur.

Particularly preferred compounds are those of the formula I wherein $R_1$ represents methoxy, ethoxy, methyl or ethyl, $R_2$ represents methoxy, ethoxy, methylamino, n-propylthio or n-propylamino, $R_3$ represents hydrogen, alkyl with 1 to 5 carbon atoms, cyclopentyl or cyclohexyl, and X represents oxygen or sulphur.

Preeminent, however, are compounds of the formula I wherein $R_1$ and $R_2$ each independently represents methoxy or ethoxy, $R_3$ represents alkyl with 1 to 5 carbon atoms, and X represents sulphur.

The compounds of the formula I can be manufactured by methods that are known per se, e.g.

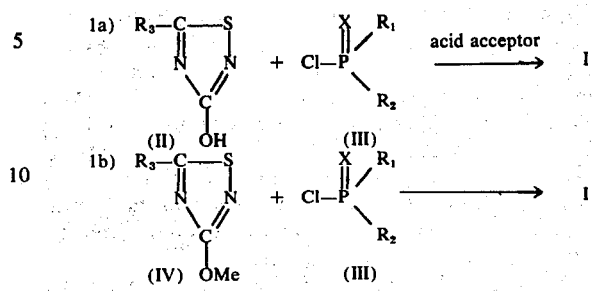

In the formula II, III and IV, the symbols $R_1$, $R_2$ and X have the meanings given for the formula I and Me represents an alkali metal in particular sodium or potassium, ammonium or alkylammonium.

Examples of suitable acid acceptors are the following bases: tertiary amines, e.g. triethylamine, dimethyl aniline, pyridine; inorganic bases, e.g. hydroxides and carbonates of alkali metals and alkaline earth metals, preferably sodium and potassium carbonate. The reactions 1a and 1b are carried out at normal pressure, at a temperature of $-10°$ to $120°C$, in particular at $+20°C$ to $80°C$, and in solvents or diluents that are inert towards the reactants. Examples of suitable solvents or diluents are: aromatic hydrocarbons, e.g. benzene, toluene; halogenated hydrocarbons, e.g. chlorobenzene, polychloro-benzenes, bromobenzenes, chlorinated alkanes with 1 to 3 carbon atoms; ethers e.g. dioxan, tetrahydrofuran; esters, e.g. ethyl acetate; ketones, e.g. acetone, methyl ethyl ketone, diethyl ketone; nitriles, e.g. acetonitrile.

The starting materials of the formulae II and IV can be manufactured by methods anologous to known ones, e.g.

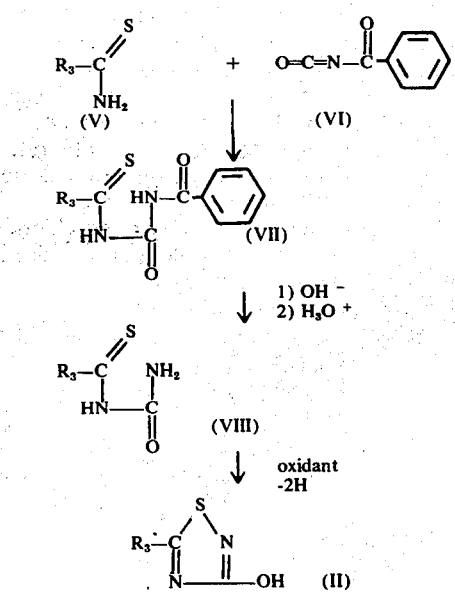

In the formulae II, V, VII and VIII, the symbol $R_3$ has the meaning given for the formula I.

Suitable oxidants are chlorine, bromine, iodine, hydrogen peroxide, peracids e.g. m-chloro-perbenzoic acid.

The reactions are carried out at normal pressure, at a temperature of −30°C to +110°C, especially at 0°–50°C, and in solvents or diluents.

Examples of suitable solvents or diluents are : aromatic hydrocarbons, e.g. benzene, toluene; halogenated hydrocarbons, e.g. chlorobenzene, polychlorobenzenes, chlorinated alkanes with 1 to 3 carbon atoms; ethers, e.g. dioxan, tetrahydrofuran, dimethoxy ethane; esters, e.g. ethyl acetate; ketones, e.g. acetone, methyl ethyl ketone, diethyl ketone; nitriles, e.g. acetonitrile; and water. The starting materials of the formulae V and VI are known and can be manufactured by methods analogous to known ones.

The compounds of the formula I can be manufactured by methods 1a or 1b by optionally combining e.g. the following starting materials of the formula II or the salts thereof of the formula IV:

3-hydroxy-1,2,4-thiadiazole
5-methyl-3-hydroxy-1,2,4-thiadiazole
5-ethyl-3-hydroxy-1,2,4-thiadiazole
5-n-propyl-3-hydroxy-1,2,4-thiadiazole
5-iso-propyl-3-hydroxy-1,2,4-thiadiazole
5-n-butyl-3-hydroxy-1,2,4-thiadiazole
5-iso-butyl-3-hydroxy-1,2,4-thiadiazole
5-sec-butyl-3-hydroxy-1,2,4-thiadiazole
5-tert.butyl-3-hydroxy-1,2,4-thiadiazole
5-n-pentyl-3-hydroxy-1,2,4-thiadiazole
5-iso-pentyl-3-hydroxy-1,2,4-thiadiazole
5-cyclopentyl-3-hydroxy-1,2,4-thiadiazole
5-cyclohexyl-3-hydroxy-1,2,4-thiadiazole
5-benzyl-3-hydroxy-1,2,4-thiadiazole with the following examples of starting materials of the formula III:

O,O-dimethyl-thiophosphoric chloride
O,O-diethyl-thiophosphoric chloride
O-ethyl-O-methyl-thiophosphoric chloride
O-methyl-methane-thiophosphonic chloride
O-ethyl-methane-thiophosphonic chloride
O-methyl-ethane-thiophosphonic chloride
O-ethyl-ethane-thiophosphonic chloride
O-propyl-ethane-thiophosphonic chloride
O-ethyl-S-propyl-dithiophospheric chloride
O-ethyl-S-sec. butyl-dithiophosphoric chloride
O-ethyl-S-n-pentyl-dithiophosphoric chlride
O-ethyl-methylamino-thiophosphoric chloride
O-ethyl-dimethylamino-thiophosphoric chloride
O-ethyl-amino-thiophosphoric chloride
O-ethyl-n-propylamino-thiophosphoric chloride
O-ehtyl-isopropylamino-thiophosphoric chloride
O,O-diethyl-phosphoric chloride Examples of such compounds are:

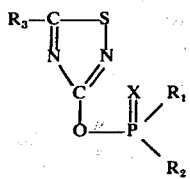

| X | $R_1$ | $R_2$ | $R_3$ |
|---|---|---|---|
| S | $OCH_3$ | $OCH_3$ | H |
| S | $OC_2H_5$ | $OC_2H_5$ | H |
| S | $C_2H_5$ | $OC_2H_5$ | H |
| S | $CH_3$ | $OC_2H_5$ | H |
| S | $CH_3$ | $OC_3H_7(n)$ | H |
| S | $OC_2H_5$ | $SC_3H_7(n)$ | H |
| S | $OC_2H_5$ | $NHCH_3$ | H |

-continued

| X | $R_1$ | $R_2$ | $R_3$ |
|---|---|---|---|
| S | $OC_2H_5$ | $NHC_3H_7(n)$ | H |
| S | $OC_2H_5$ | $NHC_3H_7(i)$ | H |
| S | $OC_2H_5$ | $NH_2$ | H |
| S | $OC_2H_5$ | $N(CH_3)_2$ | H |
| O | $OC_2H_5$ | $SC_3H_7(n)$ | H |
| S | $OC_2H_5$ | $OC_2H_5$ | $C_2H_5$ |
| S | $OC_2H_5$ | $OC_2H_5$ | $C_3H_7$ (n) |
| S | $OC_2H_5$ | $OC_2H_5$ | $C_4H_9(n)$ |
| S | $OC_2H_5$ | $OC_2H_5$ | $C_4H_9$ (i) |
| S | $OC_2H_5$ | $OC_2H_5$ | $C_4H_9$ (sec.) |
| S | $OC_2H_5$ | $OC_2H_5$ | $C_4H_9$ (tert.) |
| S | $OC_2H_5$ | $OC_2H_5$ | $C_5H_{11}$ (n) |
| S | $OC_2H_5$ | $OC_2H_5$ | $C_5H_{11}$ (i) |
| S | $OC_2H_5$ | $OC_2H_5$ | cyclopentyl |
| S | $OC_2H_5$ | $OC_2H_5$ | cyclohexyl |
| S | $OC_2H_5$ | $OC_2H_5$ | Phenethyl |
| S | $OCH_3$ | $OCH_3$ | $CH_3$ |
| S | $OC_2H_5$ | $OC_2H_5$ | $CH_3$ |
| S | $C_2H_5$ | $OC_2H_5$ | $CH_3$ |
| S | $CH_3$ | $OC_2H_5$ | $CH_3$ |
| S | $CH_3$ | $OC_3H_7(n)$ | $CH_3$ |
| S | $OC_2H_5$ | $S_3H_7(n)$ | $CH_3$ |
| S | $OC_2H_5$ | $NHCH_3$ | $CH_3$ |
| S | $OC_2H_5$ | $NHC_3H_7$ (n) | $CH_3$ |
| S | $OC_2H_5$ | $NHC_3H_7$ (i) | $CH_3$ |
| S | $OC_2H_5$ | $NH_2$ | $CH_3$ |
| S | $OC_2H_5$ | $N(CH_3)_2$ | $CH_3$ |
| O | $OC_2H_5$ | $SC_3H_7$ (n) | $CH_3$ |
| S | $OCH_3$ | $OC_3H$ | $C_3H_7$ (i) |
| S | $C_2H_5$ | $OC_2H_5$ | $C_3H_7$ (i) |
| S | $CH_3$ | $OC_2H_5$ | $C_3H_7$ (i) |
| S | $CH_3$ | $OC_3H_7$ (n) | $C_3H_7$ (i) |
| S | $OC_2H_5$ | $SC_3H_7$ (n) | $C_3H_7$ (i) |
| S | $OC_2H_5$ | $OC_2H_5$ | $C_3H_7$ (i) |
| S | $OC_2H_5$ | $NHCH_3$ | $C_3H_7$ (i) |
| S | $OC_2H_5$ | $NHC_3H_7$ (n) | $C_3H_7$ (i) |
| S | $OC_2H_5$ | $NHC_3H_7$ (i) | $C_3H_7$ (i) |
| S | $OC_2H_5$ | $NH_2$ | $C_3H_7$ (i) |
| S | $OC_2H_5$ | $N(CH_3)2$ | $C_3H_7$ (i) |
| O | $OC_2H_5$ | $SC_3H_7$ (n) | $C_3H_7$ (i) |

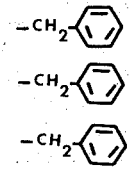

| S | $OCH_3$ | $OCH_3$ | $-CH_2-\langle\bigcirc\rangle$ |
| S | $OC_2H_5$ | $OC_2H_5$ | $-CH_2-\langle\bigcirc\rangle$ |
| S | $C_2H_5$ | $OC_2H_5$ | $-CH_2-\langle\bigcirc\rangle$ |

The compounds of the formula I have a broad biocidal activity and can be used for combating a variety of plant and animal pests.

In particular they are suitable for combating insects of the families:

Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coocinellidae, Bruchidae, Scarabaeidae, Dermestidae, Tenebrionidae, Curculionidae, Tineidae, Noctuidae, Lymantriidae, Paralidae, Galleriidae, Culicidae, Tipulidae, Stomoxydae, Muscidae, Calliphoridae, Trypetidae, Pulicidae, as well as Acaridae of the families: Ixodidae, Argasidae, Tetranychidae, Dermanyssidae.

By addition of other insecticides and/or acaricides it is possible to improve substantially the insecticidal or acaricidal action and to adapt it to given circumstances.

Examples of suitable additives are: organic phosphorus compounds, nitrophenols and derivatives thereof; pyrethrines; formamidines; ureas; carbamates and chlorinated hydrocarbons.

In addition to the above mentioned properties, the compounds of the formula I are also active against representatives of the order Thallophyta. Thus a number of these compounds display bactericidal action. But they are active chiefly against fungi, especially against phytopathogenic fungi belonging to the following classes: Oomycetes, Zygomycetes, Ascomycetes Basidiomycetes, Denteromycetes.

The compounds of the formula I also exhibit a fungitoxic action against fungi which attack the plants from the soil. The new active substances are also suitable for treating seeds, fruit, tubers etc. from attack by fungus infections. The compounds of the formula I are also suitable for combating phytopathogenic nematodes.

The compounds of the formula I may be used as pure active substance or together with suitable carriers and/or additives. Suitable carriers and additives can be solid or liquid and correspond to the substances conventionally used in formulation technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances can take, and be used in, the following forms:

Solid forms:
  dusts, scattering agents, granules coated granules, impregnated granules and homogeneous granules.
Liquid forms:
  a. concentrates of active substances which are dispersible in water: wettable powders, pasts, emulsions:
  b. solutions.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

a.
  5 parts of active substance
  95 parts of talcum
b.
  2 parts of active substance
  1 part of highly disperse silicic acid
  97 parts of talcum.

The active substances are mixed with the carriers and ground.

Granules

The following substances are used to produce 5% granules:
  5 parts of active substance,
  0.25 parts of epichlorohydrin,
  0.25 parts of cetyl polyglycol ether,
  3.50 parts of polyethylene glycol,
  91 parts of kaolin (particle size 0.3–0.8 mm)

The active substance is mixed with epichlorohydrin and dissolved with 6 parts of acetone; the polyethylene glycol and cetyl polyglycol ether are then added. The resulting solution is sprayed on kaolin, and the acetone is subsequently evaporated in vacuo.

Wettable powder

The following constituents are used for the preparation of (a) a 40%, (b) and (c) a 25%, and (d) a 10% wettable powder:

a.
  40 parts of active substance,
  5 parts of sodium lignin sulphonate,
  1 part of sodium dibutyl-naphthalene sulphonate,
  54. parts of silicic acid.
b.
  25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate,
  19.5 parts of silicic acid,
  19.5 parts of Champagne chalk,
  28.1 parts of kaolin.
c.
  25 parts of active substance,
  2.5 parts of isooctylphenoxy-polyoxyethylene-ethanol,
  1.7 parts of Champagne chalk/hydroxyethyl cellulose mixture (1:1),
  8.3 parts of sodium aluminium silicate,
  16.6 parts of kieselguhr,
  46 parts of kaolin,
d.
  10 parts of active substance,
  3 parts of a mixture of the sodium salts of saturated fatty alcohol sulphates,
  5 parts of naphthalenesulphonic acid/formaldehyde condensate,
  82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a.
  10 parts of active substance,
  3.4 parts of epoxidised vegetable oil,
  13.4 parts of a combination emulsifier consisting of fatty alcohol polyglycol ether and alkyl-aryl sulphonate calcium salt,
  40 parts of dimethylformamide,
  43.2 parts of xylene,
  25 parts sof active substance,
  2.5 parts of epoxidised vegetable oil,
  10 parts of an alkylarylsulphonate/fatty alcoholglycol ether mixture,
  5 parts of dimethylformamide,
  57.5 parts of xylene.

From these concentrates it is possible to produce, by dilution with water, emulsions of any desired concentration.

Spray

The following constituents are used to prepare a 5% spray:
5 parts of active substance,
1 part of epichlorohydrin,
94 parts of benzene (boiling limits 160°C–190°C).

EXAMPLE 1 a. Manufacture of the compound of the formula

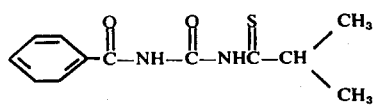

A mixture of 59 g of the compound of the formula

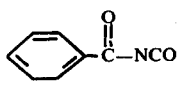

and 41.2 g of the compound of the formula

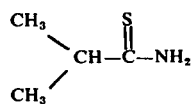

in 450 ml of absolute benzene are heated to reflux temperature over the course of 2 hours. The reaction mixture is cooled to 17°C and the crystalline precipitated product is filtered off and dried, to yield the compound of the formula

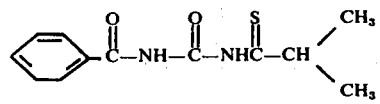

with a melting point of 170°–190°C (with decomp.).

b. Manufacture of the compound of the formula

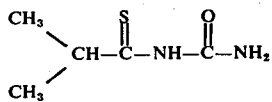

A mixture of 50 g of the compound of the formula

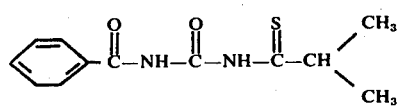

and 32 g of 100 % sodium hydroxide solution are stirred in 100 ml of acetone and 400 ml of water for 10 hours at room temperature. The reaction mixture is subsequently adjusted to pH 6 with 40 ml of glacial acetic acid at 15°C. The crystallised product is filtered off, washed with water and dried, to yield the compound of the formula

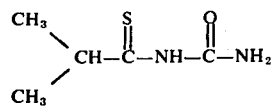

as pale yellow crystals with a melting point of 153°C.

c. Manufacture of the compound of the formula

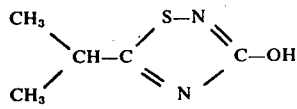

14.6 g. of the compound of the formula

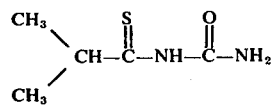

and 21.2 g of triethylamine are dissolved in 150 ml of dimethoxy ethane. To this solution are added dropwise 16.8 g $Br_2$ in 20 ml of carbon tetrachloride at 10°C over the course of 15 minutes. The mixture is stirred for 1 hour and the white precipitate is then filtered off and the filtrate concentrated. 100 ml of a mixture of n-hexane and ethyl acetate (4:1) are added to the residue. The solution is separated from the insoluble residue and cooled to −30°C. The crystalline precipitated product is filtered off, washed and dried, to yield the compound of the formula

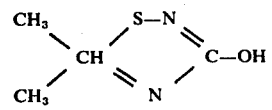

with a melting point of 67°–69°C.

Manufacture of
O,O-diethyl-O-[5-isopropyl-1,2,4-thiadiazolyl-(3)]-thiophosphate 14.5 g of 3-hydroxy-5-isopropyl-1,2,4-thiadiazole are dissolved in 250 ml of toluene at 50°C and 18.9 g of chlorothiophosphoric diethyl ester are added to the solution. Then 11.1 g of triethylamine are added, the mixture is stirred for 6 hours at 50° to 60°C, and the resulting triethylamine hydrochloride is then filtered off. The product is evaporated and chromatographed on silica gel to give the active substance of the formula

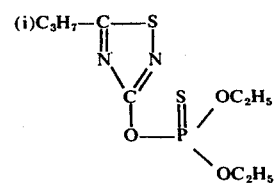

as a pale yellow oil with a refractive index of $n_D^{23} = 1.5020$.

The following compounds were also manufactured in analogous manner:

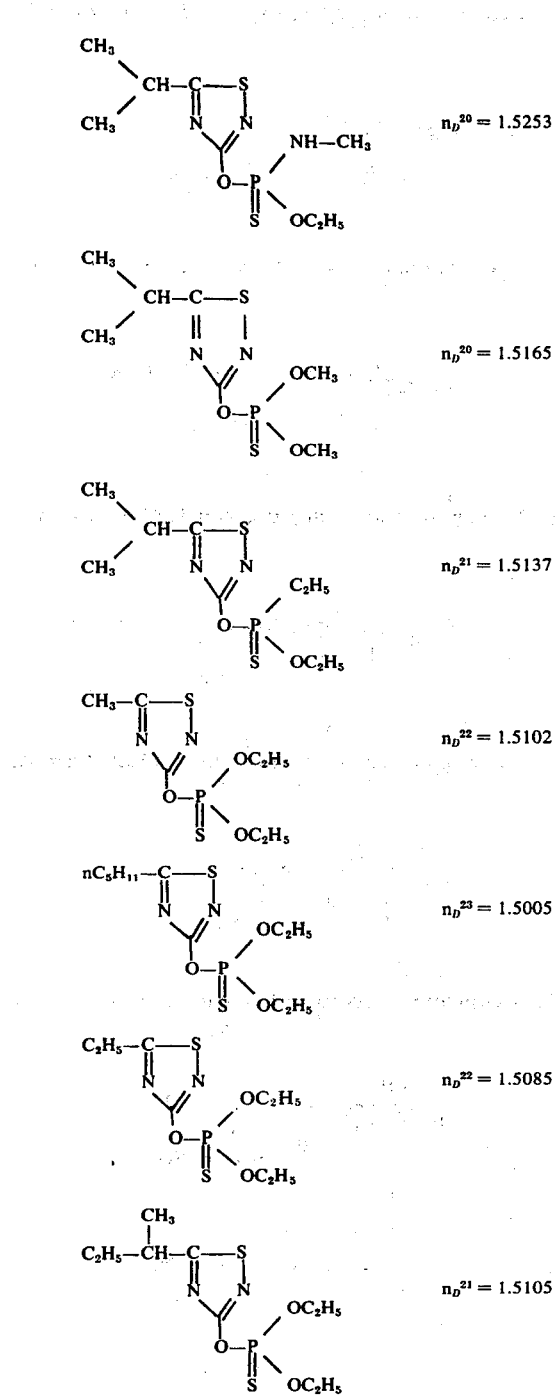

EXAMPLE 2

A. Insecticidal ingest poison action

Cotton and potato plants were sprayed with a 0.05% aqueous emulsion (obtained from a 10% emulsifiable concentrate). After the coating had dried, the cotton plants were populated with Spodoptera littoralis or Heliothis virescens larvae $L_3$ and the potato plants with Colorado potato betle larvae (Leptinotarsa Decemlineata). The test was carried out at 24°C and 60% relative humidity. In the above test, the compounds according to Example 1 displayed good ingest poison action against Spodoptera littoralis, Heliothis and Leptinotarsa decemlineata.

EXAMPLE 3

Action against Chilo suppressalis

Six rice plants at a time of the variety Caloro were transplanted into plastic pots (diameter at the top = 17 cm) and reared to a height of about 60 cm. Infestation with Chilo suppressalis larvae ($L_1$ : 3–4 mm long) took place 2 days after the active substance had been applied in granule form to the paddy water (rate of application: 8 kg of active substance per hectare). Evaluation of the insecticidal action took place 10 days after application of the granules.

The compounds according to Example 1 were active in the above test against Chilo suppressalis.

EXAMPLE 4

Action against ticks

A. Rhipicephalus bursa

Five adult ticks and 50 tick larvae were counted into a glass tube and immersed for 1 to 2 minutes in 2 ml of an aqueous emulsion from a dilution series each containing 100, 10, 1 and 0.1 ppm of test substance. The tube was then sealed with a cotton-wool plug and placed on its head, so that the active substance emulsion could be absorbed by the cotton-wool.

In the case of the adults evaluation took place after 2 weeks, and in that of the larvae after 2 days. Each test was repeated twice.

B. Boophilus microplus (larvae)

Tests were carried out with 20 OP-sensitive and 20 OP-resistant larvae respectively using an analogous dilution series as in the case of Test A. (The resistance refers to the tolerability of Diazinon).

The compounds according to Example 1 acted in these tests against adults and larvae of Rhipicephalus bursa and OP-sensitive and OP-resistant larvae of Boophilus microplus.

EXAMPLE 5

Acaracidal action

Phaseolus vulgaris (dwarf beans) had an infested piece of leaf from a mass culture of Tetranychus urticae placed on them 12 hours before the test for the acaricidal action.

The mobile stages which have migrated were sprayed with the emulsified test preparations from a chromatography atomiser so that the sprayed preparation did not run off. The number of living and dead larvae, adults and eggs were evaluated after 2 to 7 days under a stereoscopic miscropscope and the result expressed in percentages. During the "interim", the treated plants were kept in greenhouse compartments at 25°C.

The compounds according to Example 1 were active in the above test against eggs, larvae and adults of Tetranychus urticae.

EXAMPLE 6

Action against soil nematodes

To test the action against soil nematodes, the active substances in the respective concentration indicated were applied to and intimately mixed with soil infected with root gall nematodes (Meloidgyne Avenaria). Immediately afterwards, tomato cuttings were planted in the thus prepared soil in a series of tests and after a waiting time of 8 days tomato seeds were sown in another test series.

In order to assess the nematocidal action, the galls present on the roots were counted 28 days after planting and sowing respectively. In this test the compounds according to Example 1 displayed good action against Meloidgyne Avenaria.

EXAMPLE 7

Sterilised compost earth was homogeneously mixed with a wettable powder containing 25% of active substance so that there resulted a rate of application of 8 kg of active substance per hectare.

Young zucchetti plants (Cucumis pepo) were put into plastic pots with the treated soil (3 plants per pot; diameter of pot = 7 cm). Each pot was infected immediately afterwards with 5 *Aulacophora femoralis and Pachmoda or Chortophila larvae. The control was carried out* 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example 1 displayed action against *Aulacophora femoralis, Pachmoda and Chortophila larvae.*

We claim:

1. A compound of the formula

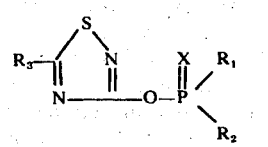

wherein $R_1$ and $R_2$ are independently methoxy or ethoxy, $R_3$ is an alkyl containing from 1 to 5 carbon atoms and X is sulfur.

2. A compound according to claim 1, of the formula

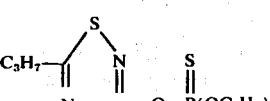

3. A compound according to claim 1, of the formula

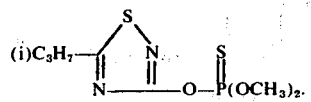

4. A compound according to claim 1, of the formula

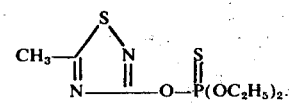

5. A compound according to claim 1, of the formula

6. A compound according to claim 1, of the formula

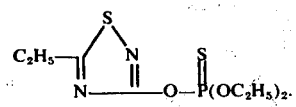

7. A compound according to claim 1, of the formula

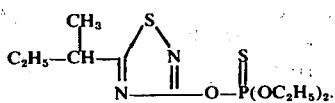

* * * * *